United States Patent [19]
Martinou et al.

[11] Patent Number: 6,022,720
[45] Date of Patent: Feb. 8, 2000

[54] BAX PROTEIN CHANNEL FORMATION

[75] Inventors: Jean-Claude Martinou; Remy Sadoul; Bruno Antonsson; Franco Conti; Gonzalo Mazzei, all of Geneva, Switzerland

[73] Assignee: Glaxo Wellcome Inc., Research Triangle Park, N.C.

[21] Appl. No.: 08/895,693

[22] Filed: Jul. 17, 1997

[51] Int. Cl.[7] .................. C12N 13/00; G01N 33/483; G01N 27/00
[52] U.S. Cl. ................... 435/173.4; 435/173.5; 435/173.7; 436/1; 436/5; 436/63; 436/149; 436/800; 436/805; 436/806; 436/808; 436/829
[58] Field of Search ............ 530/350; 435/173.4, 435/173.5, 173.7; 436/149, 800, 805, 806, 808, 829, 1, 5, 63

[56] References Cited

PUBLICATIONS

Korsmeyer et al, Bcl–2 Gene Family in Development and Oncogenesis, Proceedings Programmed Cell Death, Oct. 1923, 1996.

Winkowski et al. Applied and Environmental Microbiology. (1996) 62/2 (323–327).

Tomita et al Journal of Biological Chemistry, Jul. 5, 1992, vol. 267, No. 19, pp. 13391–13397.

Zalman et al Infection and Immunity Dec. 1985, vol. 50 (3) 630–635

Shin et al Biochimica et Biophysica Acta, Jul. 19, 1979, vol. 555 (1) 79–88.

*Primary Examiner*—Paula K. Hutzell
*Assistant Examiner*—Geetha P. Bansal
*Attorney, Agent, or Firm*—Nixon & Vanderhye P.C.

[57] ABSTRACT

The present invention relates, in general, to a protein that regulates programmed cell death and, in particular, to the pro-apoptotic protein, Bax, which forms channels in lipid membranes. The invention further relates to methods of identifying agonists and antagonists of Bax channel formation and/or activity and thereby agents that can be used therapeutically to promote or inhibit cell death.

41 Claims, 10 Drawing Sheets

↓
GSPGIPDGSG EQPRGGGPTS SEQIMKTGAL LLQGFIQDRA
∇
GRMGGEAPEL ALDPVPQDAS TKKLSECLKR IGDELDSNME

LQRMIAAVDT DSPREVFFRV AADMFSDGNF NWGRVVALFY

FASKLVLKAL CTKVPELIRT IMGWTLDFLR ERLLGWIQDQ

GGWDGLLSYF GTPTWQTVTI FVAGVLTASL TIWKKMG
⇧

Fig. 2

BAX PROTEIN CHANNEL FORMATION

TECHNICAL FIELD

The present invention relates, in general, to a protein that regulates programmed cell death and, in particular, to the pro-apoptotic protein, Bax, which forms channels in lipid membranes. The invention further relates to methods of identifying agonists and antagonists of Bax channel formation and/or activity and thereby agents that can be used therapeutically to promote or inhibit cell death.

BACKGROUND

Apoptosis or programmed cell death is a form of active cell death essential during the development and maintenance of tissue homeostasis and for the elimination of damaged cells (Saunders, Science 154:604 (1996); Kerr et al, Br. J. Can. 26:239 (1972)). Apoptotic cell death is also involved in a wide range of pathological conditions including cancer and immunological and neurodegenerative diseases (McDonnell, Mol. Carcinogen 8:209 (1993); Camilleri-Broert et al, Blood 86:432 (1995); Migheli et al, Neuroreport 15:1906 (1994)). Regulation of the apoptotic process involves the activation of intracellular proteins, including proteins of the Bcl-2 family. Bcl-2 was first identified as an inhibitor of apoptosis following its identification in follicular B-cell lymphoma (Tsujimoto et al, Science 228:1440 (1985); Vaux et al, Nature 335:440 (1988)). The members of the Bcl-2 family exhibit either anti-apoptopic (Bcl-2, Bcl-xl, Mcl1, Ced9) or pro-apoptotic (Bax, Bak, Bad, Bcl-Xs) properties (Korsmeyer, Trends 11:101 (1995)). It has been proposed that the activity of the proteins is regulated through the formation of homo- and hetero-complexes (Borner et al, Biochem. Cell Biol. 72:463 (1994); Farrow et al, Curr. Opin. Gen. Dev. 6:45 (1996)). One model, the rheostat model, proposes that the homo-complex of Bax induces downstream death activators and the hetero-complex with Bcl-2 inactivates Bax by preventing homo-complex formation (Oltavai et al, Cell 74:609 (1993)). The equilibrium between homo- and hetero-complexes can be regulated either at the transcriptional level or through post-translational modifications, in particular, phosphorylation. Bcl-2 phosphorylation has been shown to modulate its ability to prevent cell death (Haldar et al, Proc. Natl. Acad. Sci U.S.A. 92:4507 (1995); Chen et al, J. Biol. Chem. 271:2376 (1996)). Bad, a pro-apoptotic member of the family, has also been shown to be phosphorylated (Zha et al, Cell 87:619 (1996)).

The proteins contain three highly conserved regions designated BH1, BH2 and BH3. The BH3 domain is essential for the death promoting activity of the pro-apoptotic proteins (Hunter et al, J. Biol. Chem. 271:8521 (1996)) whereas BH1 and BH2 are required for the formation of protein complexes (Borner et al, Biochem. Cell Biol. 72:463 (1994); Farrow et al, Curr. Opin. Gen. Dev. 6:45 (1996)). The proteins have the potential of being membrane attached and contain a predicted membrane spanning domain at the COOH-terminus which gives the proteins a low solubility once extracted from their natural environment. Bcl-2 has been shown to be predominantly localized to the mitochondrial outer membrane, but the protein also is found in the endoplasmic reticulum and the nuclear membrane (Krajewski et al, Cancer Res. 53:4701 (1993)). Recently, Bax and Bcl-$x_L$ were shown to translocate from the cytosolic fraction to the membrane fraction when apoptosis was induced in murine thymocytes (Hsu et al, Proc. Natl. Acad. Sci. U.S.A. 94:3668 (1997)). In HeLa cells, overexpressed Bax is localized predominantly to the mitochondrial and the endoplasmic reticulum membranes.

Recently, the X-ray and NMR structures of Bcl-$x_L$ were solved (Muchmore et al, Nature 381:335 (1996)). The $\alpha$ helical structures present in bacteria toxins, colicins and diphteria toxin, which are believed to be associated with their pore-forming activity, are apparently conserved in Bcl-$X_L$ (where they are coded for by the amino acids linking the BH1 and BH2 domains) thereby suggesting that Bcl-$X_L$ may have pore-forming activity. Indeed, Bcl-$x_L$ was subsequently shown to form ion channels in synthetic lipid membranes (Minn et al, Nature 385:353 (1997)).

Although Bcl-$x_L$ and Bax belong to the same protein family they have opposite activities; Bcl-$x_L$ anti-apoptotic activity and Bax pro-apoptotic activity. Indeed, the amino acid sequence identity between Bcl-$x_L$ and Bax is only 26% with the highest homologies in the BH1–3 domains. Moreover, the sequence between the BH1 and BH2 domains coding for the putative pore-forming $\alpha$ helices in Bcl-$x_L$ is not at all conserved in Bax. The present invention results from the finding that, despite the opposite activities, relatively low sequence homology and lack of conservation of the region between BH1 and BH2, Bax, like Bcl-$x_L$, has channel-forming activity.

SUMMARY OF THE INVENTION

The present invention is based on the finding that Bax protein forms channels in lipid membranes and the invention relates to methods of identifying agonists and antagonists of Bax channel formation and/or activity. Agonists and antagonists so identified can be used in the treatment of diseases and disorders, including neurodegenerative diseases and neoplasia.

Objects and advantages of the invention will be clear from the description that follows.

BRIEF DESCRIPTION OF THE DRAWINGS

FIG. 1A. Lane 1, crude supernatant; lane 2, protein bound to the Glutathione-Sepharose; lane 3, protein eluted by thrombin cleavage from the Glutathione-Sepharose; lane 4, pool from the Heparin-Sepharose; lane 5, pool from the DEAE-Sepharose; lane 6, molecular weight markers.

FIG. 2. Amino acid sequence of the Bax protein. The conserved domains, from the $NH_2$-terminus BH3, BH1 and BH2, are underlined. ↓ indicates the start of the Bax sequence preceded by 6 amino acids from the cloning vector. ↑ indicates the end of the $Bax_{66\,c}$ protein. ∇ indicates the trypsin cleavage site.

FIG. 3A. Gel filtration analysis of $Bax_{Ac}$. $Bax_{Ac}$ was diluted to 15 mM in 25 mM Tris-HCl, 0.2 mM DTT, 300 mM NaCl, 2% octyl glucoside, pH 7.5, and analyzed on a Superdex 200 column on the Pharmacia SMART system. The protein eluted mainly as a complex of 200,000 kDa (12.2 min) with a small amount at 26,000 kDa (16.5 min.), presumably corresponding to monomeric $Bax_{Ac}$.

FIG. 5A. Autoradiographs of the gels after phosphorylation with MAP kinase for 10 and 60 min, PKA for 10 and 60 min, PKG for 10 and 60 min, $p34^{cdc2}$ for 10 and 60 min.

FIG. 6A. Survival of neurons microinjected with cDNAs encoding Bcl-2 or Bcl-2 lacking last 34 amino acids. FIG. 6B. Survival of neurons microinjected with cDNAs encoding Bax or Bax lacking last 20 amino acids. FIG. 6C. SDS-PAGE of Bax and Bcl-2.

FIG. 7A. Effect of 10 $\mu$M Bax on neurons. FIG. 7B. Effect of 5 $\mu$M Bax on neurons. FIG. 7C. Effect of 10 $\mu$M Bcl-2 on neurons. FIG. 7D. Effect of Bax and Bcl-2 on sheep red blood cells.

FIG. 8A. Concentration-dependent induction of dye efflux from liposomes by Bax. FIG. 8B. Inhibition of Bax-induced carboxyfluorescein efflux by Bcl-2. FIG. 8C. Effect of pH on Bax-induced carboxyfluorescein efflux from liposomes. FIG. 8D. Effect of pH on channel-forming ability of Bcl-2.

FIG. 9A. Continuous recording of small single channel currents induced by 20 nM Bax added to both sides of a diphyPC planar bilayer with symmetric 125 mM-NaCl solutions at pH 7. The applied voltage ($V_m$) was 100 mV. Data were sampled at 4 KHz but are shown low-pass filtered at 40 Hz. The mean open-channel conductance is 5.6±0.2 pS. At 1 KHz bandwidth the opening time showed a rapid flickering with a mean open-time of 3.5±0.2 ms and a poorly quantifiable close-time (<1 ms). FIGS. 9B–C. A 90 s continuous recording of Bax channel activity in conditions similar to FIG. 9A at an applied $V_m$ of –50 mV. * FIG. 9C. The histogram shows a conductance level of 250±25 pS (*). Other peaks represent levels of lower amplitude of 180±25 ↓, 80±25 (↓) and 26±7 (+) pS. The dwell time at any level above 125 pS was fitted by a single exponential distribution with a mean time of 240±20 ms. FIG. 9D. Large steps of membrane conductance recorded during 30 s at –60 mV. The largest conductance level is approximately 1.6 nS, the predominant level is 700 pS. Several other conductance levels in steps of approximately 450 pS and 900 pS are readily observable. Smaller openings at the beginning and the end of the trace have characteristics similar to those shown in FIGS. 9B–C. FIGS. 9E–F. A 80 s continuous recording of single channel activity at pH 4 of the type shown in FIG. 9B for pH 7. 150 nM Bax was added on both sides at an applied $V_m$ of 100 mV. The data were analyzed after low-pass filtering at 200 Hz. FIG. 9F the histogram shows two main conductance levels at 77±10 pS (*) and 27±4 pS (↓) and two minor small conductance channels (8.5±1 pS and 4±2 pS). The dwell time at any level above 40 pS was fitted by a single exponential distribution with a mean time of 85±6 ms (note the difference in time scale between FIGS. 9B–C and 9E–F). FIG. 9G. Incorporation or formation of Bax channels is facilitated by negative voltages when applied to the side to which the protein was added. The traces show the average response to a series of 30 voltage pulses according to the double step protocol shown in the upper part of the panel. In the experiment with Bax in trans the voltage steps were ±40 mV, while in the other experiment the voltage steps were ±60 mV.

DETAILED DESCRIPTION OF THE INVENTION

Figure 1A:
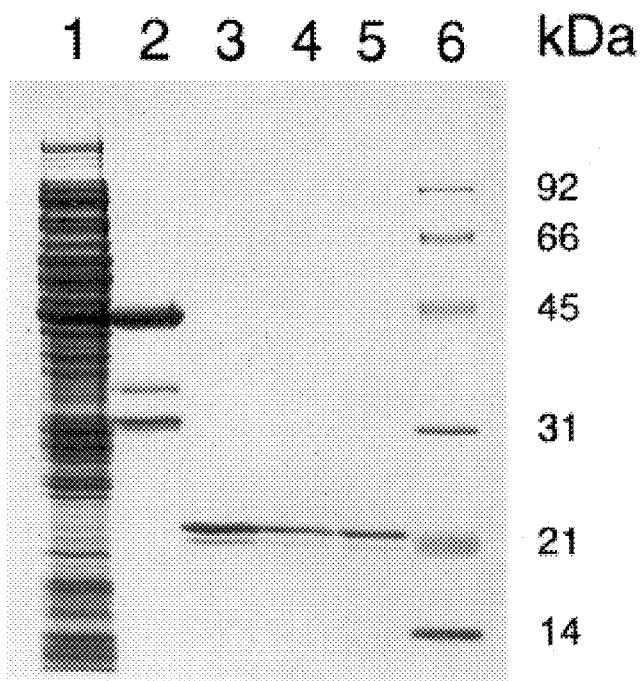
FIGS. 1A and B. Purification of $Bax_{66\,c}$. Samples from the various purification steps were analyzed on 14% SDS-PAGE (14% Novex gels in a SDS buffer system) and proteins were detected by Coomassie staining.

A basis for the present invention is the finding that the pro-apoptotic protein Bax inserts into lipid membranes and forms channels therethrough. At least 2 Bax molecules appear necessary for channel formation. Seven or more Bax molecules may be preferred (see Example II). The channel forming properties of Bax are pH dependent and distinct from those of the anti-apoptotic proteins Bcl-x and Bcl-2. At normal physiological pH, Bax channel forming activity is, in fact, antagonized by Bcl-2. While not wishing to be bound by theory, Bcl-2 may exert its effect on Bax channel forming activity by forming a heteropore with Bax protein.

Demonstration of Bax channel forming activity makes possible assays that can be used to identify compounds that specifically modulate channel formation and/or channel activity, which compounds can be used therapeutically to enhance or inhibit Bax-mediated cell lysis. Bax channel blockers can be used, for example, in the treatment of diseases/disorders of the nervous system associated with neuronal apoptosis, including traumatic brain injury, spinal cord injury, neurodegenerative diseases, reperfusion injury, myocardial infarction and cerebral ischemia. Enhancers of Bax channel formation or channel activity can be used, for example, in the treatment of diseases/disorders such as neoplasia, autoimmune diseases, transplant rejection and lymphoproliferative diseases.

Assays suitable for screening compounds for their ability to inhibit or augment the membrane channel forming activity of Bax can take any of a number of forms. Membranes appropriate for use in such assays include naturally occurring cellular membranes (eg membranes of mammalian cells or membrane preparations from such cells), membranes from cell organelles and synthetic membranes. Particularly useful cellular membranes include those of neuronal cells and of red blood cells. Particularly useful membranes from organelles include those from mitochondria. Suitable synthetic membranes include planar lipid bilayers or liposomes (see Examples V and VI).

Forms of Bax protein suitable for use in the assays of the invention include intact Bax protein, preferably mammalian Bax protein, more preferably human Bax protein, and modified, channel-forming forms thereof. Soluble forms of the protein that retain activity are advantageous due to ease of handling. One such soluble form is Bax protein devoid of the hydrophobic C-terminal region, eg, the last 20 amino acids (see the Examples). (As used in this section, "Bax protein" includes intact Bax protein and modified (eg soluble) forms thereof that form channels.)

In one embodiment, the assay comprises contacting a lipid membrane with Bax protein under conditions (ie, pH etc) such that the protein can insert into the membrane and form pores therethrough. The contacting is effected in the presence and absence of a compound to be tested for its ability to modulate channel formation or channel activity, and the results compared. Typically, the test compound is contacted with the lipid membrane first and then Bax protein added. However, Bax protein can be first contacted with the lipid membrane and the channel formed before addition of the test compound. (This latter approach can permit identification of compounds that affect activity (ie function) of an existing channel.) Alternatively, the Bax protein and test compound can be added simultaneously.

The effect of a test compound can be established, for example, by monitoring the passage of a material from one side of the lipid membrane to the other, wherein the passage is, at least in part, Bax channel-dependent. Advantageously, the material is a readily detectable material such as a dye, eg a fluorescent dye (for example, a dye large enough to be retained by the lipid membrane in the absence of channels but small enough to pass through the channels once formed, eg, carboxyfluorescein or derivative thereof).

A preferred form of this embodiment of the invention utilizes liposomes encapsulating a fluorescent dye. Upon contacting the liposomes with Bax protein and channel formation, dye is released, that release being detectable. A dye such as carboxyfluorescein can be encapsulated in the liposomes at a concentration above that at which its natural fluorescence quenches. With passage of dye the through the Bax channels, fluorescence in the solution surrounding the liposomes increases. The effect of a test compound on Bax channel formation (or activity) can be determined by comparing the rate fluorescence increases (eg the rate the dye is released) in the presence and absence of the test compound. A delayed rate of dye release in the presence of the test compound is indicative of a compound that blocks Bax channel formation or activity. An accelerated rate of dye release is indicative of a compound that enhances channel formation or activity.

In another embodiment, the ability of a test compound to modulate Bax channel formation and/or activity is determined by adding Bax protein at a toxic concentration to a culture of cells (eg neurons or erythrocytes), in the presence and absence of a test compound, and monitoring Bax-induced cell lysis. A delay in cell lysis in the presence of the test compound is indicative of a Bax channel blocker while an increase in cell lysis or lysis rate is indicative of a compound that enhances channel formation or activity. Alternatively, the ability of a compound to enhance Bax channel formation/activity can be determined by adding Bax at a non-toxic concentration to a culture of cells, in the presence and absence of the test compound. A test compound that enhances channel formation/activity results in cell toxicity or lysis.

In yet another embodiment of the invention, the effect of a test compound on channel formation/activity is determined electrophysiologically using, for example, a lipid bilayer. One such approach is described in Example VI.

The invention also includes assays suitable for screening compounds for their ability to inhibit or enhance the formation of a Bax/Bcl-2 heteropore. Such assays can be structured like those described above with the exception that Bcl-2, in addition to Bax protein, is used.

Compounds identified as Bax channel modifiers can be formulated, for example, with a pharmaceutically acceptable carrier, diluent or excipient. Compositions so produced can be used to treat diseases/disorders including those enumerated above. The dose to be administered will vary depending on the compound, the mode of administration, the patient and the effect sought. Optimum doses and preferred regimens can be established readily.

The invention further relates to kits suitable for use in screening compounds for Bax channel formation/activity modulating activity. In one aspect, the kit comprises Bax protein and lipid membrane components (eg phospholipids), for example, disposed within container means. The kit can also include ancillary reagents, including those required for lipid membrane formation.

Further aspects of the invention are described in greater detail in the non-limiting Examples that follow.

EXAMPLE I

Expression and Purification of Soluble Recombinant Human Bax

To obtain soluble human Bax, the protein was truncated of the 20 amino acid hydrophobic domain at the COOH-terminus ($Bax_{Ac}$).

Methodology

Specifically, full length human Bax α cDNA was used for PCR amplification of the Bax sequence without the 20 amino acid hydrophobic COOH-terminal domain. At the 5' end the primer sequence 5'-CCG <u>GAATTC</u>CTGACGGGTCCGGGGAGCAG-3' and at the 3' end the primer sequence 5'-CCG <u>GAATTC</u>TTAGGTCTGCCACGTGGGCGTCCC-3' were used. The primers introduced EcoR1 restriction enzyme sites which are underlined. The PCR DNA fragment was isolated using the QIAquick kit (Qiagen) and digested with EcoR1. The EcoR1 fragment was subcloned into the EcoR1 site of the pGEX2T plasmid from Pharmacia. The purified plasmid was transformed into *E. coli* cell line PR745 and the cells were propagated at 37° C. Transformants were isolated by selection for ampicillin resistance in the presence of 0.5% glucose. Resistant clones were tested for GST-$Bax_{Ac}$ expression by growing the cells to an $OD_{600}$ of 0.6 in the presence of 0.5% glucose and inducing GST-$Bax_{Ac}$ expression by addition of 1 mM IPTG and further growing the cells for 2.5 h. The cells were harvested and GST-Bax$_{66\ c}$ expression was analyzed by SDS-PAGE. To confirm the correct sequence of the inserted PCR fragment plasmid mini preparation was performed from the clones shown to express GST-Bax$_{Ac}$ and the DNA was sequenced.

A single colony of the transfected *E. coli* strain was grown in 800 ml LB inoculum in shaker flask. The inoculum was transferred into a 50 liter working volume fermenter (Chemap/MBR, Switzerland). Medium and conditions were as described by Bernard et al (Chapter 5.2 in "Current Protocols in Protein Science" (Coligan, J. E. et al, eds) J. Wiley, New York (1995)). The culture was grown to an OD$_{650}$ of approximately 10 and expression of the fusion protein was induced by addition of IPTG to a final concentration of 1 mM. The culture was further incubated for 5 h and at the end of the incubation the cells were harvested by continuous flow centrifugation (Sharples, France). The bacteria yield was typically 40 g/l (wet weight).

The cell paste (100 g) was suspended in 3 volumes of lysis buffer (100 mM Tris-HCl, 100 mM NaCl, 2 mM MgCl$_2$, 1 mM DTT, 1 mM EDTA, 1 mM PMSF, 1 mM benzamidine, 1% Triton X-100, 10 μg/ml antipain and soybean trypsin inhibitor, 2 μg/ml each pepstatin A, aprotinin, α$_1$-antitrypsin and leupeptin, pH 8.5), lysozyme 0.1 mg/ml and DNAse I 50 μg/ml were added. The cells were broken by passage through a French press cell twice at a cell pressure of 16,000 psi. The sample was centrifuged at 35,000×g for 30 min and GST-Bax$_{Ac}$ was recovered in the supernatant. The supernatant was mixed with 30 ml Glutathione-Sepharose equilibrated in lysis buffer and the suspension was rotated at 4° C. for 30 min. The gel suspension was transferred to a column and washed with 400 ml lysis buffer, 200 ml of washing buffer (50 mM Tris-HCl, 50 mM KCl, 20 mM MgCl$_2$, 5 mM ATP, pH 8.0) followed by 200 ml thrombin buffer (50 mM Tris-HCl, 150 mM NaCl, 2.5 mM CaCl$_2$, 0.1 mM DTT, pH 8.0). Bax$_{Ac}$ was eluted from the column through cleavage by thrombin. Thrombin buffer containing 0.3 units/ml of thrombin was pumped over the column at a flow rate of 0.3 ml/min over night. The eluate from the column was passed over a 1 ml Benzamidine-Agarose column before being collected in tubes containing 200 μl of 0.1 mM benzamadine (10 ml/fraction). The fractions containing Bax$_{Ac}$ were pooled (450 ml) and dialyzed against 25 mM Tris-HCl, 50 mM NaCl, 1 mM DTT, 1 mM PMSF, 1 mM benzamidine, pH 8.0. The dialyzed pool was applied to a 50 ml Heparin-Sepharose column equilibrated in 25 mM Tris-HCl, 50 mM NaCl, 1 mM DTT, 1 mM PMSF, 1 mM benzamidine, pH 8.0, and Bax$_{Ac}$ was collected in the flow thorough fractions. The pool from the Heparin-Sepharose column was further purified on a 50 ml DEAE-Sepharose column equilibrated in 25 mM Tris-HCl, 50 mM NaCl, 1 mM DTT, 1 mM PMSF, 1 mM benzamidine, pH 8.0. The column was developed with a 20 column volume linear gradient of 50 to 350 mM NaCl in 25 mM Tris-HCl, 1 mM DTT, 1 mM PMSF, 1 mM benzamidine, pH 8.0. Fractions containing Bax$_{Ac}$ were pooled, dialyzed against 25 mM Tris-HCl, 0.2 mM DTT, 30% glycerol, pH 7.5, concentrated in an Amicon pressure concentrator using a PM10 membrane and stored at –80° C.

Results

Initial attempts to isolate *E. coli* transformants expressing Bax$_{Ac}$ failed presumably due to its toxic effect on the bacteria. It was found, however, that transformants could be obtained when the protein was expressed as a GST fusion protein in the pGEX2T vector and the bacteria were grown in the presence of 0.5% glucose. Glucose was required to suppress the tac promotor and eliminate a low leakage expression of the fusion protein. The soluble cell fraction, from which GST-Bax$_{Ac}$ protein was isolated, contained approximately half of the expressed fusion protein. Including 1% Triton X-100 in the solubilization buffer increased the amount of the fusion protein in the soluble cell fraction. The Bax$_{Ac}$ protein released from the fusion protein by thrombin cleavage was over 80% pure on SDS-PAGE, further purification being effected on Heparin-Sepharose followed by DEAE-Sepharose (FIG. 1A). Bax$_{Ac}$ did not bind to the Heparin-Sepharose column but some of the contaminating proteins were removed. The protein eluted with the salt gradient (200–250 mM NaCl) from the DEAE column was close to homogeneously pure on SDS-PAGE. Typical yields of pure Bax$_{Ac}$ were 50 mg/100 g of wet cells.

EXAMPLE II

Characterization of Soluble Human Bax Protein

Figure 1B:
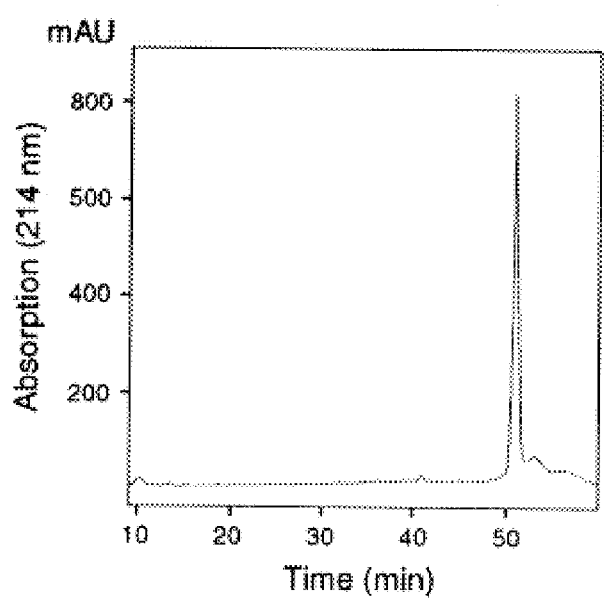
FIG. 1B. The pool from the DEAE-Sepharose analyzed on reversed phase HPLC eluted with a linear gradient of 0–80% acetonitrile in 0.1% trifluoroacetic acid.

The identify of the protein resulting from purification described in Example I was confirmed by NH$_2$-terminal amino acid sequencing. Bax$_{Ac}$ started with six amino acids (GSPGIP . . . ) from the expression plasmid followed by the Bax sequence ( . . . DGSGEQ . . . ) (FIG. 2). In the purified Bax$_{Ac}$ preparation a protein approximately 1 kDa smaller than Bax$_{Ac}$ could also be detected. This protein is seen as a weak band below Bax$_{Ac}$ on the SDS-PAGE (FIG. 1A). Attempts to remove this protein from the Bax$_{Ac}$ preparation by chromatography on Phenyl-Sepharose, hydroxylapatite, MonoQ and gel filtration were all unsuccessful. Amino acid sequencing showed that the protein had the Bax$_{Ac}$ NH$_2$-terminal sequence. This suggests that during the purification a small amount of the Bax$_{Ac}$ protein was cleaved internally at the COOH-terminus giving rise to a 1 kDa smaller protein. RP-HPLC analysis showed that Bax$_{Ac}$ constituted over 94% and the cleavage product approximately 4% in the purified Bax$_{Ac}$ preparation (FIG. 1B). The Bax$_{Ac}$ protein contained 177 amino acids and had a calculated molecular weight of 19,444 Da. Electrospray ionization mass spectrometry gave a molecular mass of 19,446±1 which shows that Bax$_{Ac}$ had not been modified during expression or purification. The spectroscopic parameters of Bax$_{Ac}$ were determined by recording absorption spectra between 200 and 300 nm and determining the concentration of the samples by amino acid analysis (for amino acid analysis, the samples were hydrolyzed in 6M HCl at 112° C. for 24 hr; the amino acids were subsequently separated on reverse phase HPLC and quantified against an internal standard of norleucine). The molar absorption coefficients were determined from the UV spectrum of a 3.4 μM Bax$_{Ac}$ solution in 25 mM Hepes-NaOH, 150 mM NaCl, pH 7.5, and were found to be $\epsilon_{280}$=39,000 M$^{-1}$×cm$^{-1}$, $\epsilon_{230}$=212,000 M$^{-1}$×cm$^{-1}$ and $\epsilon_{220}$=341,000 M$^{-1}$×cm$^{-1}$.

Figure 3A:
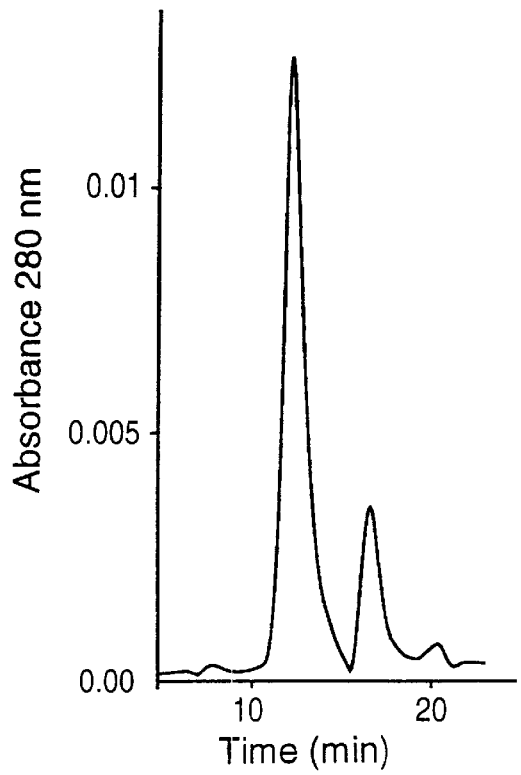
FIGS. 3A and B. Gel filtration and equilibrium centrifugation analysis of $Bax_{Ac}$.

The purified Bax$_{Ac}$ was analyzed at a flow rate of 75 μl/min on a Superdex 200 column on the SMART system from Pharmacia. The column was equilibrated and run in 25 mM Tris-HCl, 300 mM NaCl, 0.2 mM DTT, pH 7.5, with or without 2% octyl glucoside. For each buffer condition the column was calibrated with gel filtration standard proteins (ferritin 440 kDa, catalase 232 kDa, aldolase 158 kDa, bovine serum albumin 67 kDa, ovalbumin 43 kDa, chymotrypsinogen A 25 kDa, ribonuclease A 13.7 kDa) from Pharmacia. When Bax$_{Ac}$ was analyzed on gel filtration in buffer without detergent, the protein migrated at a molecular weight larger than 400,000 Da. In the presence of 2% octyl glucoside, most of the protein eluted at a molecular weight of 200,000 Da with a small amount eluting at 26,000 Da (FIG. 3A). The smaller peak presumably corresponds to monomeric $Bax_{Ac}$ and the larger peak to a complex of 6–10 $Bax_{Ac}$ molecules.

Figure 3B:
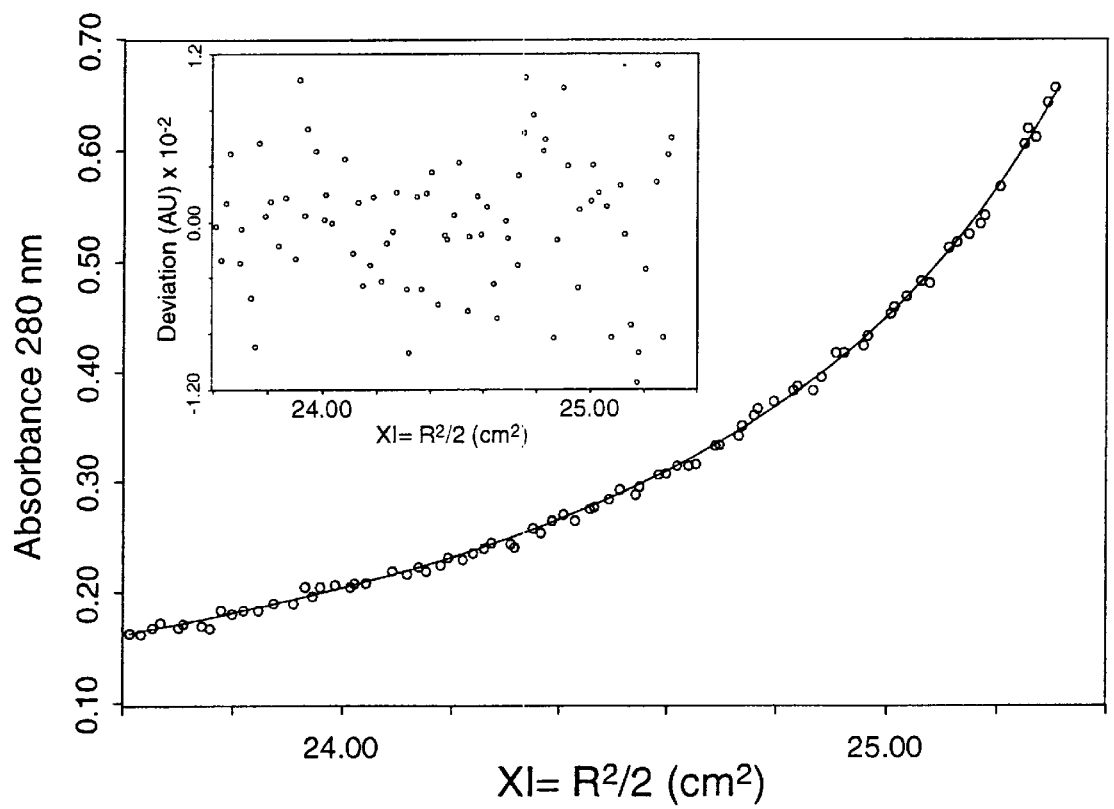
FIG. 3B. Sedimentation equilibrium analysis of $Bax_{Ac}$. A representative sedimentation equilibration data set of $Bax_{\Delta c}$ at an initial concentration of 10.6 $\mu$M centrifuged at 6,300 rpm at 4° C. until equilibrium was reached. The solid line represents the best fit of the data to a 1-2-4 model, where 1 represents an heptamer, 2 a dimer of heptamers and 4 a tetramer of heptamers. The insert presents the residual plot of the data to the model.

To determine the composition of the larger $Bax_{Ac}$ complex, the protein was analyzed by sedimentation equilibrium centrifugation (FIG. 3B). Sedimentation equilibrium experiments were performed in a Beckman Optima XL-A analytical ultracentrifuge equipped with absorbance optics, using an An60Ti rotor and three sample cells each with a six-sector charcoal filled epoxy centerpiece. Samples in 50 mM Tris, 100 mM NaCl, 1 mM β-mercaptoethanol, pH 7.5, at protein concentrations between 1.3 μM and 40.2 μM were centrifuged against buffer blanks at 4° C. at 5000, 6300 and 9200 rpm and allowed to spin for 12 hours prior to data collection. Ten individual data sets per speed were collected at 2 hour intervals and these were the average of 10 scans taken at 280 nm with a step size of $3 \times 10^{-3}$ cm in a step mode. Equilibrium was ascertained by comparing data sets up to 20 hours apart. The density (ρ=1.00709 g/ml) was measured on a Paar DMA58 density meter calibrated against air and water. The partial specific volume of the protein ($v_{25}$=0.736891 ml/g) was calculated by the method of Cohn et al (Chapter 4 "Proteins, amino acids and peptides as ions and dipolarions" (Rheinhold ed), New York (1943)) and adjusted to the correct temperature ($v_4$=0.727966 ml/g) as described in Durchschlag (Chapter 3, "Thermodynamic data for biochemistry and biotechnology (Hinzed) Springer-Verlag, New York (1986)). Data sets were edited with REEDIT (Jeff Lary, National Analytical Ultracentrifugation center, Storrs, Conn., U.S.A.) and fit individually and jointly with NONLIN (Johnson et al, Biophys. J. 36:575 (1981)). NONLIN fits the data to an effective reduced molecular weight, $\sigma=M(1-v\rho)\omega^2/RT$ where M is the molecular weight, v is the partial specific volume of the protein, ρ is the solvent density, $\omega=(2 \pi(rpm)/60)$, R is the gas constant and T is the temperature in Kelvin. Data from different speeds and concentrations were combined for a global fit. The smallest observed particle was equivalent to 7 monomers and thus a was fixed to a heptamer when fitting to an association scheme. The calculated extinction coefficient $\epsilon_{280}$=31, 130 $M^{-1}$ $cm^{-1}$ for a Bax monomer was used to estimate the heptamer value which was assumed to be $2.179 \times 10^5$ $M^{-1}$ $cm^{-1}$. The data were best fitted to a 1-2-4 model, where 1, represents a heptamer; 2, a dimer of heptamers and 4, a tetramer of heptamers. Attempts were made to force the fits to penta-, hexa- or octa-mers but the errors ruled out these possibilities. Including monomers or smaller species in the fit gave no improvement and were also dismissed. Centrifugations performed in the presence of 1 M NaCl did not change the distribution of species suggesting that the interactions are not of ionic nature. These results show a clear difference between Bax and the anti-apoptotic proteins Bcl-2 and Bcl-$x_L$ which are both present as monomers in solution (Muchmore et al, Nature 381:335 (1996); Vance et al, J. Biol. Chem. 271:0811 (1996)).

Bcl-$x_L$ and Bcl-2 have been shown to form pores in lipid membranes (Minn et al, Nature 385:353 (1997); Schondel et al, Proc. Natl. Acad. Sci. U.S.A. 94:5113 (1997)). The Examples that follow show that $Bax_{Ac}$ can also form pores in lipid membranes. The heptameric and monomeric solution structure might indicate a difference in the pore forming structure of the pro- and anti-apoptotic proteins of the Bcl-2 protein family. The Bax heptamer formation explains why it was not possible to remove the small amount of COOH-terminal cleaved $Bax_{Ac}$ from the purified preparation (FIG. 1A). The cleaved molecules may be part of heptamer complexes, and not separate as individual molecules on chromatography.

Figure 4:
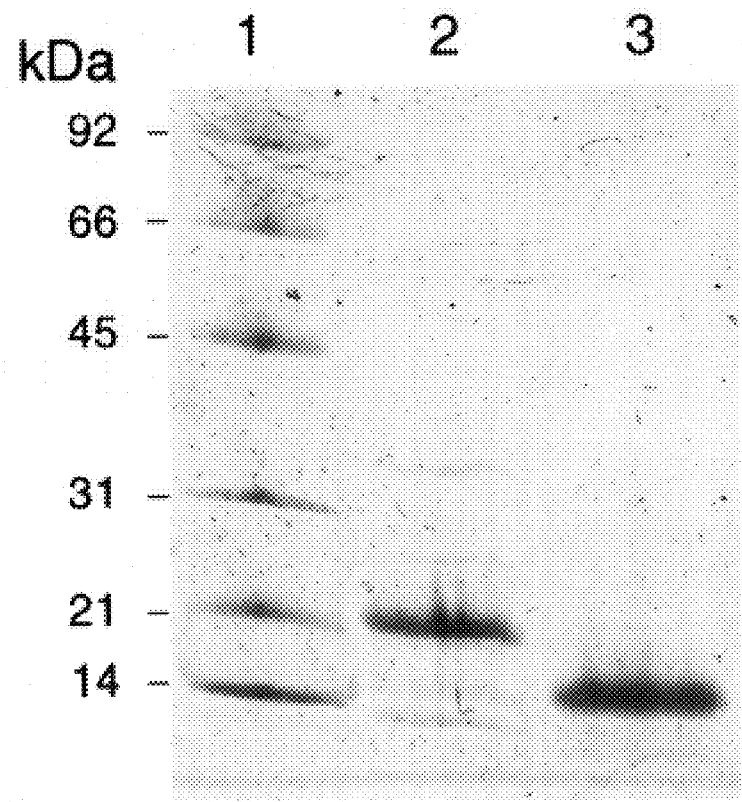
FIG. 4. Limited trypsin digestion of $Bax_{\Delta c}$. 200 $\mu$g $Bax_{\Delta c}$ in 25 mM Tris-HCl, 150 mM NaCl, 2.5 mM $CaCl_2$, 0.1 mM DTT, pH 7.5 was digested with 0.3 $\mu$g trypsin at 4° C. for 30 min. The digestion was stopped by addition of 20 $\mu$g of soybean trypsin inhibitor. The sample was analyzed on a 10–15% SDS-PAGE and proteins were detected by Coomassie staining. Lane 1, molecular weight markers; lane 2, $Bax_{\Delta c}$ incubated without trypsin; lane 3, $Bax_{\Delta c}$ incubated with trypsin.

Limited trypsin digestion of $Bax_{Ac}$ produced a specific protein fragment of approximately 15 kDa (FIG. 4). $NH_2$-terminal amino acid sequencing of the fragment showed that it had been generated by cleavage after arginine 42 in the $Bax_{Ac}$ sequence (FIG. 2). The trypsin-cleaved Bax eluted as a heptamer complex on gel filtration in the presence of octyl glucoside. Although the amino acid homology between Bax and Bcl-2 is not high in this region, the trypsin cleavage site is located approximately 25 amino acids $NH_2$-terminal of the conserved BH3 domain in both proteins (see Vance et al, J. Biol. Chem. 271:30811 (1996)). This indicates that although Bax does not have the extensive loop structure found in Bcl-$x_L$ (see Muchmore et al, Nature 381:335 (1996)) this region of the protein is exposed and accessible to proteolytic attack.

Figure 5:
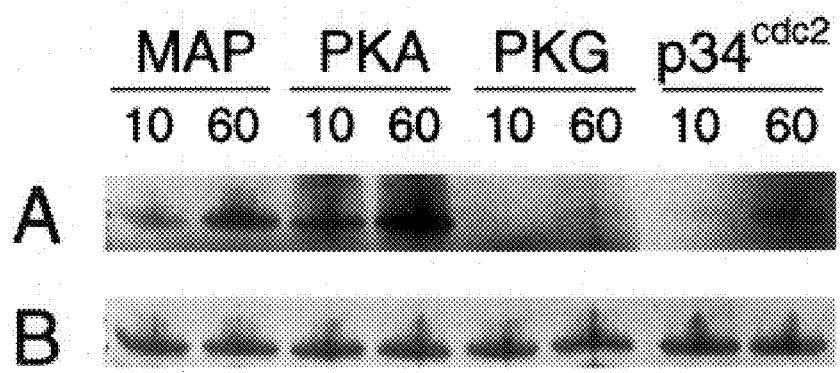
FIGS. 5A and B. Phosphorylation of $Bax_{\Delta c}$. Purified $Bax_{\Delta c}$ was dialyzed into 25 mM Hepes-NaOH, 150 mM NaCl, 0.1 mM DTT, pH 7.5. For each phosphorylation assay, 50 pmols (1 $\mu$g) of protein was employed in buffers as described below. As a control, 1 $\mu$g myelin basic protein was phosphorylated in parallel. The total reaction volumes were 10 $\mu$l. MAP-kinase (p44mpk): 10 ng MAP-kinase in 15 mM MOPS, pH 7.0, 10 mM $MgCl_2$, 0.5 mM EGTA, 50 mM NaF and 1 mM DTT. cAMP-dependent protein kinase (PKA): 5 mU PKA in 20 mM MOPS, pH 7.0, 10 mM $MgCl_2$, 0.5 mM EDTA and 1 mM DTT. cGMP-dependent protein kinase (PKG): 20 units cGMP dependent kinase in 40 mM Tris-HCl, pH 7.5, 20 mM $Mg(C_2H_3O_2)_2$, 0.1 mM EDTA and 2 mM cGMP. $p34^{cdc2}$ kinase: 10 units $p34^{cdc2}$ in 20 mM MOPS, pH 7.0, 10 mM $MgCl_2$, 1 mM EGTA, 50 mM NaF, and 0.5 mM DTT. All reaction mixtures contained 0.2 mM $[\gamma^{33}P]$-ATP at 2.5 Ci/mmol. The samples were incubated at 35° C. for 10 or 60 min. At the end of the incubation period, the reactions were stopped by addition of 1 volume of SDS electrophoresis sample buffer and the samples were heated at 95° C. for 5 min. The samples were analyzed on 10–15% gradient PhastGels from Pharmacia, the gels were stained, dried and autoradiographed. After 10 and 60 min. incubation, 10 pmols were withdrawn, mixed with one volume SDS-PAGE sample buffer and heated at 95° C. for 5 min. The samples were analyzed on 10–15% SDS-PAGE Phastgel, the gels were stained, dried and autoradiographed.
FIG. 5B. Coomassie staining of the gels to show that an equal amount of $Bax_{\Delta c}$ was used in all assays.

Phosphorylation has been suggested as a possible mechanism for regulating the activity of the Bcl-2 family proteins. A determination was thus made as to whether $Bax_{Ac}$ could be phosphorylated in vitro by serine/threonine kinases. The protein was phosphorylated by cAMP dependent protein kinase (PKA) and to an apparent lesser degree by p34$^{cdc2}$ kinase and MAP p42 kinase (FIG. 5A). No phosphorylation was detected with cGMP dependent protein kinase (PKG). The Coomassie staining of the PAGE in FIG. 5B shows that equal amounts of protein were used in all assays. Under the same assay conditions the control protein myelin basic protein (MBP) was phosphorylated to approximately the same degree by all four kinases. At least in vitro Bax is a substrate for specific serine/threonine kinases which indicates that the activity of Bax can be regulated by phosphorylation.

EXAMPLE III

Figure 6A:
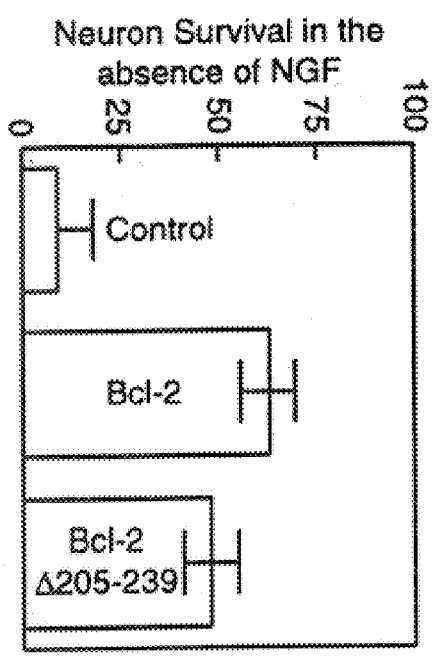
FIGS. 6A–C. Characterization and purification of biologically active Bax and Bcl-2 lacking the hydrophobic COOH-terminal domain.

Purification and Characterization of Biologically Active Bax and Bcl-2 Lacking the Hydrophobic COOH-Terminal Domain Purification:

Human Bcl-2 lacking 34 amino acids at the COOH terminus was expressed in *E. coli* and purified from the soluble cell fraction by sequential chromatography on Q Sepharose, Phenyl-Sepharose, Heparin-Sepharose and FPLC Omon Q). The purified proteins were analyzed on 10 to 15% SDS-polyacrylamide gel electrophoresis (PAGE) gradient gels on the PhastSystem from Pharmacia (see FIG. 6C). Proteins were detected by Coomassie blue staining. The identity of the proteins was confirmed by $NH_2$-terminal amino acid sequencing and by mass spectrometry. Lane 1, Bax; lane 2, Bcl-2.

Characterization:

Sympathetic neurons were microinjected with cDNAs (Garcia et al, Science 258:302 (1992); Martinou et al, J. Cell Biol. 128:201 (1995)) encoding either Bcl-2 or Bcl-2 lacking the last 34 amino acids. Twenty four hours later nerve growth factor (NGF) was withdrawn from the culture medium. Neuron survival was assayed after 48 hours of NGF-deprivation and is expressed as the percentage of neurons at 6 hours after injection (neurons that survived injection). The results are presented in FIG. 6A and represent mean±SEM for n=3 with 100 to 150 neurons injected in each experiment.

Figure 6B:
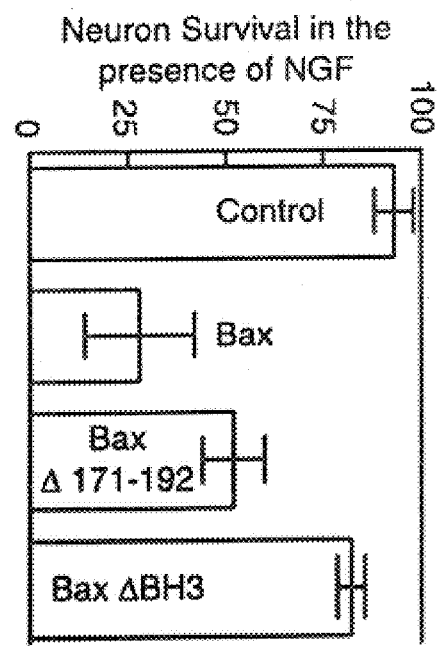
Figure 6C:
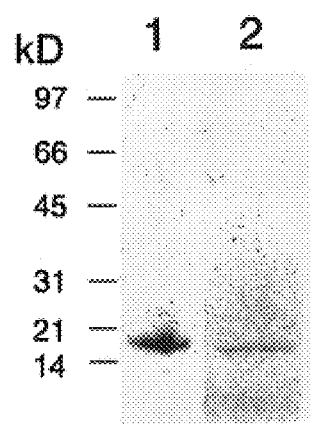

Neurons were also microinjected with cDNAs encoding either Bax or a Bax mutant lacking the last 20 amino acids (prepared as described in Example I above) Neuron survival was assayed 48 hours later. The results shown in FIG. 6B are mean +SEM for n=3 with 100 to 150 neurons injected in each experiment.

EXAMPLE IV

Lytic Effects of Bax on Neurons and Red Blood Cells

Figures 7A, 7B, 7C:
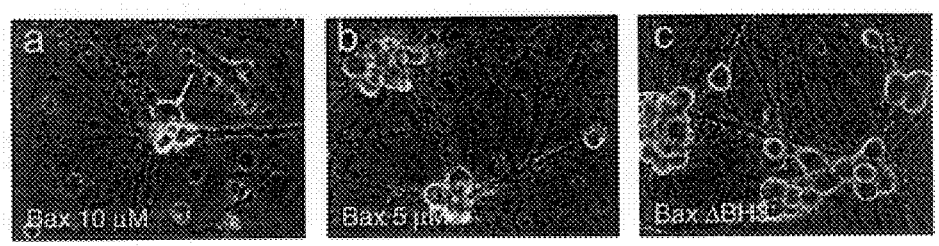
FIGS. 7A–D. Lytic effects of Bax on neurons and red blood cells.

The effect of soluble recombinant Bax and Bcl-2 on the integrity of sympathetic neurons and sheep erythrocytes was tested. Ten $\mu$M Bax protein was added to serum-free medium of sympathetic neurons. Three to six hours later, neurons began to swell and finally lysed (see arrow of FIG. 7A). When 5 $\mu$M Bax was added under the same conditions, neurons became granular and died after 24 hrs. (see FIG. 7B). These data indicated that below a critical Bax concentration, neurons could compensate for the toxic effects of Bax. Addition of 10 $\mu$M Bax together with an equimolar amount of Bcl-2 delayed neuronal lysis approximately 12 hrs (n=2) while no effect was observed upon coaddition of control proteins (ERK2 or stathmin). This result is consistent with an apparent decrease in Bax concentration indicating neutralization by Bcl-2.

Figure 7D:
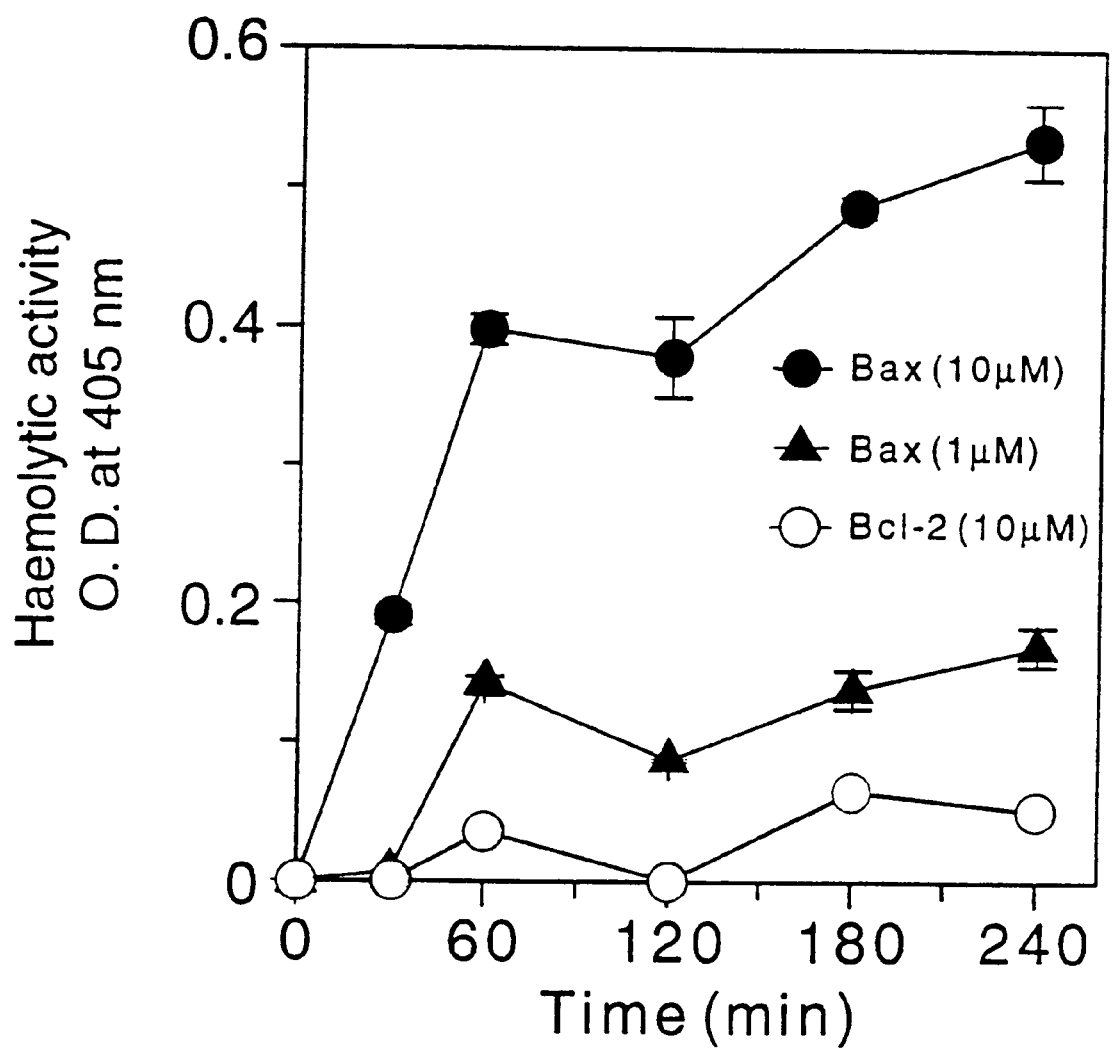

Bax (10 $\mu$M), Bax (1 $\mu$M) and Bcl-2 (10 $\mu$M) were added to sheep red blood cells and incubated at 37° C. in TBS, 10 mM Tris-HCl, pH 7.4, 155 mM NaCl, 5 mM KCl, 0.5 mM $CaCl_2$ under continuous shaking and hemoglobin release was measured at different time points (Kenny et al, Mol. Microbiol. 11:99 (1994)). Ten $\mu$M Bax caused lysis (FIG. 7D). In contrast, addition of Bcl-2 had no deleterious effect on neurons (FIG. 7C) or red blood cells (FIG. 7D), indicating the membrane interacting properties of these two proteins are intrinsically different.

EXAMPLE V

Release of Liposome-Encapsulated Carboxyfluorescein

To determine whether Bax was a pore-forming protein, a study was undertaken to determine whether Bax could trigger the release of liposome-encapsulated carboxyfluorescein. Liposomes containing 20 mM 6,7 carboxyfluorescein (Sigma) were prepared as described by Sadoul et al (Nature 304:347 (1983)) using 400 $\mu$g phosphatidylserine from bovine brain (Sigma), 400 $\mu$g phosphatidylcholine (Sigma) and 230 $\mu$g of cholesterol (Fluka). The liposomes were dialyzed for 24 hours against PBS and diluted to 8 ml. For analysis at acidic pH, fluorescence of released dye was measured after adjustment of pH to 7.5 by addition of 1 M Tris-HCl pH 7.5.

Figure 8A:
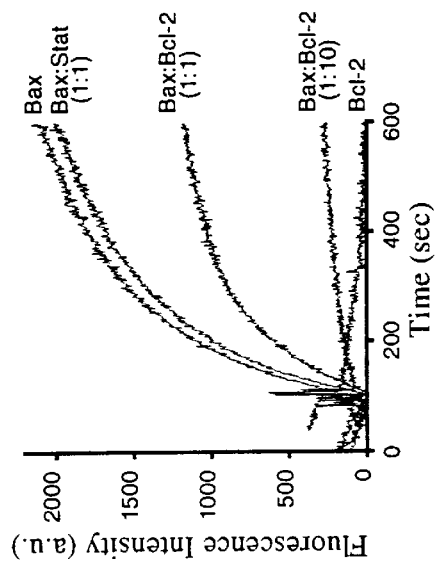
FIGS. 8A–D. Release of liposome-encapsulated carboxyfluoresceine.

Fluorescence was measured every second with a spectrofluorimeter (Jasco; FP-777) with excitation at 488 nm and emission at 520 nm. In each test 20 $\mu$l of liposomes containing 20 mM carboxyfluorescein was diluted in 1 ml of PBS (pH 7.5) and 5 $\mu$l of purified protein was added at the time indicated by the arrow. Incubation was performed at room temperature. Final Bax concentrations are indicated for each curve (see FIG. 8A). Bcl-2 was tested at 70 nM. Each curve of FIG. 8A was normalized by subtraction of the initial fluorescence value obtained at time 0. As shown in FIG. 8A, Bax induced dye efflux from liposomes in a concentration-dependent manner at neutral pH, with a maximal effect at 120 nM. Under the same conditions, Bcl-2 triggered no carboxyfluorescein release at concentrations up to 360 nm.

Channel formation by bacteria toxins, colicins, diptheria toxin, Bcl-2 and Bcl-x is favored by low pH (Minn et al, Nature 385:353 (1997)). Thus a determination was made of the ability of Bax and Bcl-2 to form pores in different pH environments. Measurements were performed in 5 mM sodium citrate, 150 mM NaCl buffers at pH 4.0, 5.0, and 6.0, and in PBS at pH 7.5. The liposomes were diluted into the buffers at 20 $\mu$l/ml and incubated for different time periods at room temperature with 2.5 nM Bax (FIG. 8C) or Bcl-2 (FIG. 8D). The background fluorescence was measured in the absence of added protein. Fluorescence measurements were performed immediately after pH neutralization of the samples by addition of 100 $\mu$l 1 M Tris-HCl, pH 7.5 (pH correction was required to eliminate fluorescence quenching at pH <7.5). The fluorescence signal is expressed as percent of total fluorescence after correction for the background. F, fluorescence in the sample; $F_0$, background fluorescence; and $F_t$, total fluorescence as measured after addition of Triton X-100.

Figure 8C:
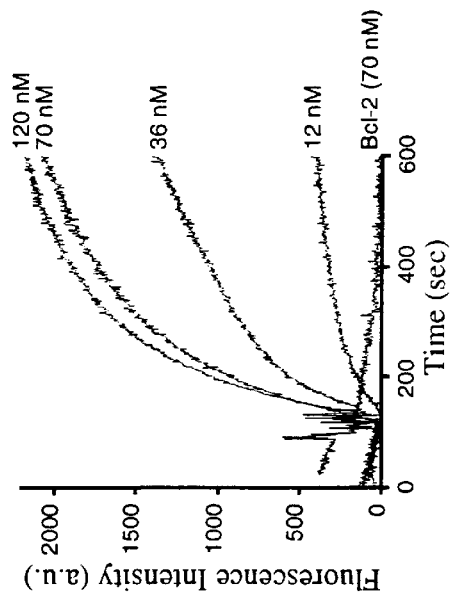
Figure 8B:
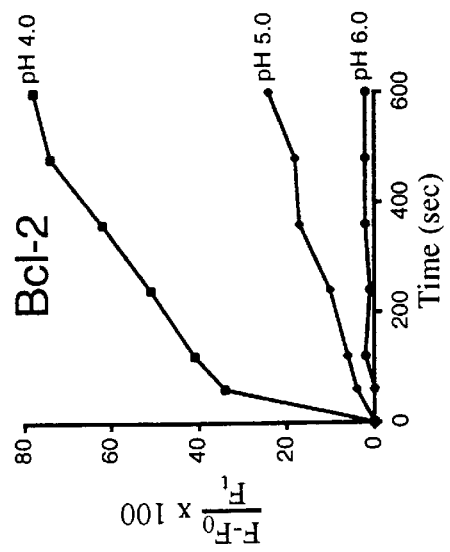
Figure 8D:
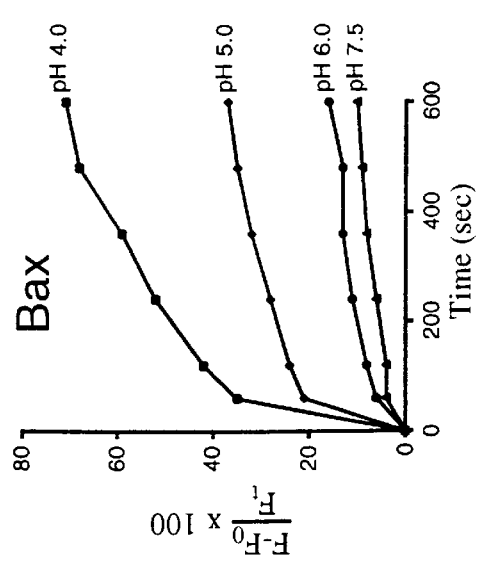

The release of carboxyfluorescein induced by 2.5 nM Bax increased in a pH-dependent manner and was eight times greater at pH 4.0 compared to pH 7.5 (FIG. 8C). In contrast, although Bcl-2 was as efficient as Bax at pH 4, the channel-forming ability of Bcl-2 decreased at pH 5 and was abrogated at pH 6 (FIG. 8D). Thus, the pore-forming properties of Bax and Bcl-2 are different.

It has been suggested that Bcl-2 antagonizes the pro-apoptotic function of Bax by blocking Bax activity (Rheostat model) (Oltvai et al, Cell 74:609 (1993)). The delay seen in Bax-induced neuronal death after coaddition of Bcl-2 supported this model and, therefore, a determination was made as to whether Bcl-2 could inhibit the Bax effect on liposomes at physiological pH. Liposomes (20 $\mu$l in 1 ml PBS) were first incubated (15 min at room temperature) with Bcl-2 or with a control protein (stathmin) before addition of Bax (70 nm) to the liposome solution. At a Bax/Bcl-2 ratio of 1:1 the Bax-triggered carboxyfluorescein efflux was decreased by 50% and at a ratio of 1:10 the efflux was almost completely inhibited (FIG. 8B). The unrelated control protein stathmin had no adverse effect on Bax function (FIG. 8B).

EXAMPLE VI

Bax Formation of Channels in Planar Lipid Bilayers

Pore formation by the Bax protein was further investigated and characterized electrophysiologically using planar lipid bilayers (see FIG. 9). Planar lipid bilayers were formed by apposition of two phospholipid monolayers initially formed at the air-water interface as described by Montal, (Meth. Enzymol. 32:545 (1974))]. The monolayers at the interface were spread from a solution of 2 mg/ml lipid (100% diphytaneoyl-phosphatidycholine (diphyPC) or 60% diphyPC, 40% phosphatidylserine in hexane). The composition of the buffered salt solutions were at pH 7.0 10 mM $NaH_2PO_4$-NaOH, 10 mM sodium citrate, 125 mM NaCl, 0.5 mM EDTA, and at pH 4.0 10 mM sodium citrate, 125 mM NaCl. Membrane currents were recorded under voltage-control using a patch-clamp amplifier (EPC-7, List, Darmstadt). Voltage stimulation and data acquisition were controlled by a Macintosh microcomputer (Cupertino, Calif.) interfaced to the recording amplifier with a 16-bit AD/DA converter (Instrutech, Elmond, N.Y.). Off-line analysis was done with special purpose programs using IGOR (Wavemetrics).

Figure 9A:
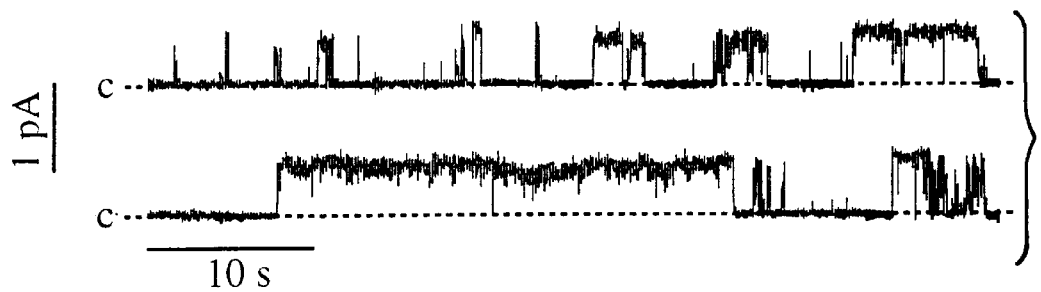
FIGS. 9A–G. Bax channel formation in planar lipid bilayers.
Figure 9B:
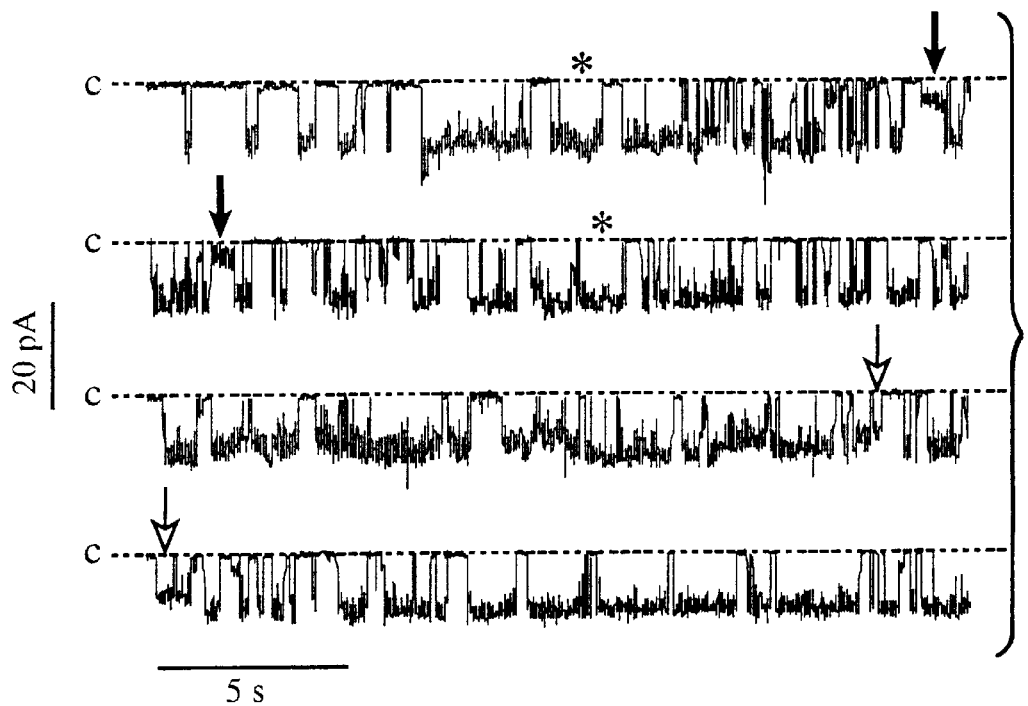
Figure 9C:
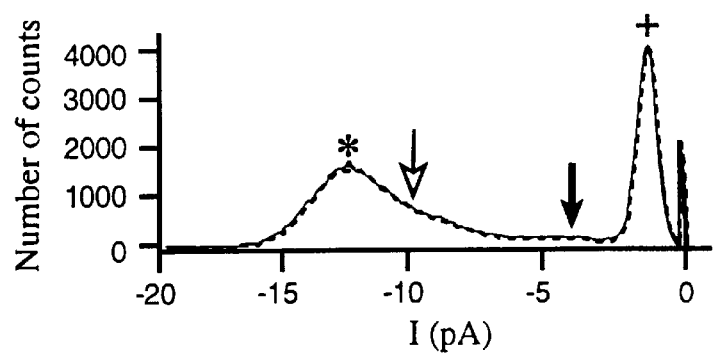
Figure 9D:
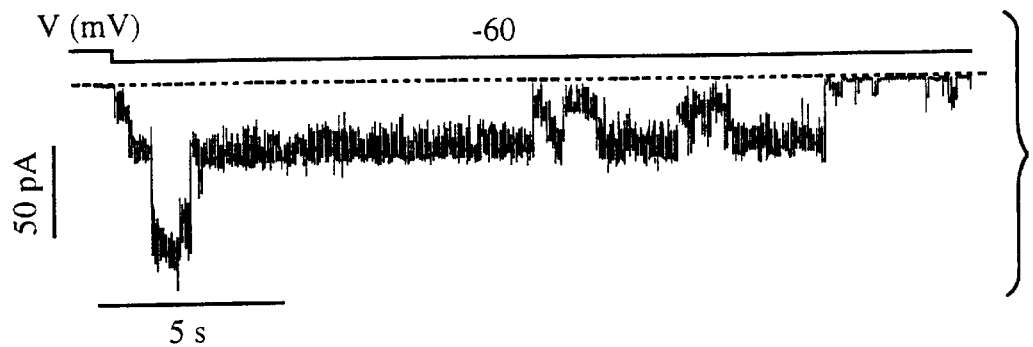

Currents were measured in bilayers (area $2 \times 10^3$ $\mu M^2$) separating symmetrical or asymmetrical salt solutions into which Bax was added at concentrations between 5 and 500 nM. Within 10 min to one hour after addition of Bax, or alternatively after membrane formation in solution containing Bax, an increase in membrane conductance ($g_m$) was consistently observed in 17 experiments performed at pH 7 and in three experiments performed at pH 4. At pH 7, elementary channels of 5.6±0.2 pS were observed occurring at early times after exposure of the membrane to Bax (observed in three experiments, FIG. 9A). The openings had a fast flickering in the ms range and their duration could not be described by a single time constant. These small pore openings were usually swamped by long bursts of larger conductance fluctuations between 26±7 pS (at 100 Hz bandwidth) and a predominant opening of 250±25 pS with occasional residencies at two main sublevels (80±25 pS and 180±25 pS) (FIGS. 9B–C). The mean dwell time ($\tau_o$) at levels above 125 pS was 240±20 ms. Further superimposed on this activity abrupt changes of $g_m$ in multiples of about 450 pS were invariably observed leading to conductances up to 2 nS (FIG. 9D). This was particularly evident at later times and with high voltages.

Figure 9E:
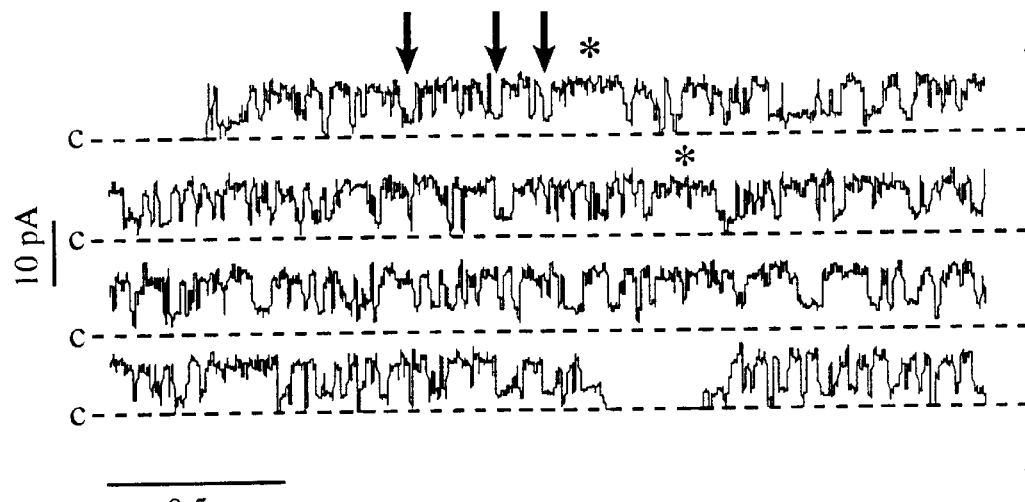
Figure 9F:
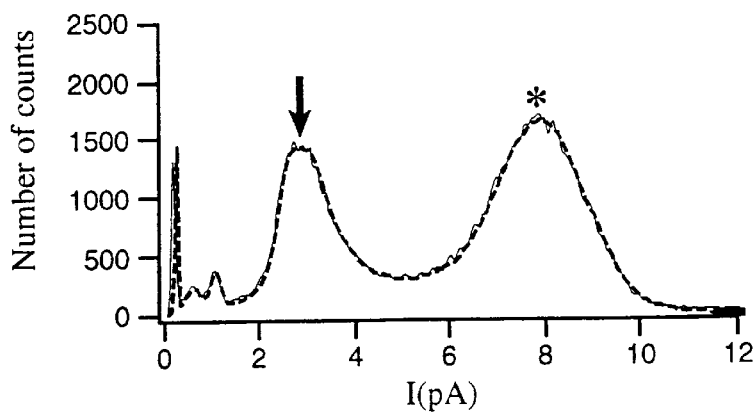

At pH 4 the Bax channel activity was modified in two main respects (FIGS. 9E–F). First, conductance levels were about 3-fold lower ($g_m$77±10 pS and 27±4 pS) and openings were much shorter-lived ($\tau_o$ above 40 pS was 85±6 ms). Large conductance changes as observed at pH 7 (FIG. 9D) were also detected at pH 4 although their levels were lower.

Figure 9G:
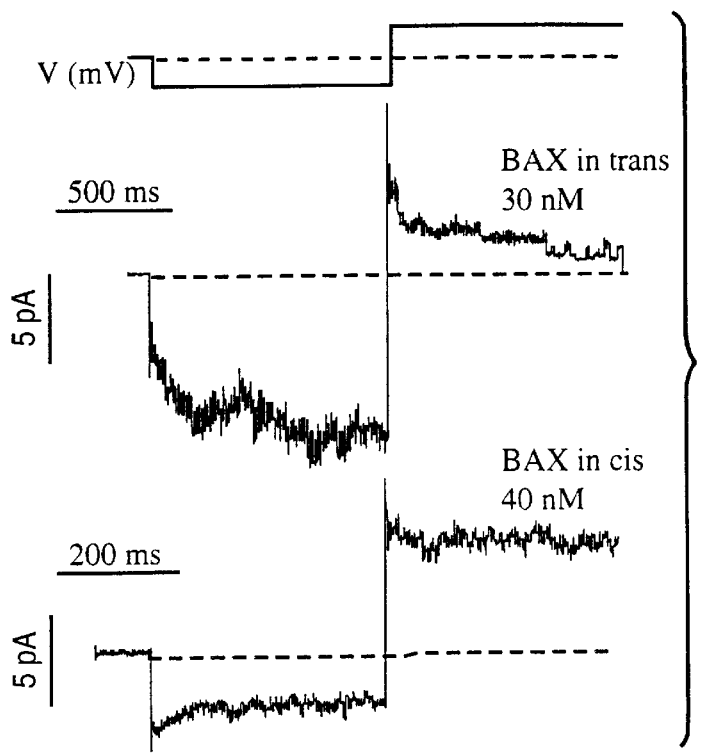

A general property of Bax channels observed under all conditions was their voltage ($V_m$)-dependent formation or activation (FIG. 9G). Interestingly, upon asymmetrical addition of Bax to one chamber, channel activity was facilitated when a negative $V_m$ was applied to the same side. However, a marked sidedness of the channel activity was also often observed when Bax was added symmetrically. This indicates that the channel forming structures have an intrinsic asymmetry.

Ion selectivity of the Bax channels at pH 7 was studied in asymmetric NaCl solutions by applying voltage ramps between −30 and +30 mV during periods of high channel activity. Two experiments with 145 mM Na$^+$ and 125 mM Cl$^-$ on the cis-side and 1M Na$^+$Cl$^-$ on the trans-side, showed a reversal potential of the channels around −15 mV, whereas in two experiments with 145 mM Na$^+$ and 125 mM Cl$^-$ on the cis-side and 40 mM Na$^+$, 20 mM Cl$^-$ on the trans-side, the reversal was estimated around +10 mV. Both estimates are consistent with channels that are slightly cation selective with a permeability ratio of Na$^+$ to Cl$^-$ of about 2.1(2.25 and 1.95 in either case).

EXAMPLE VII

Effect of Bax Channel Blocker

Figure 10:
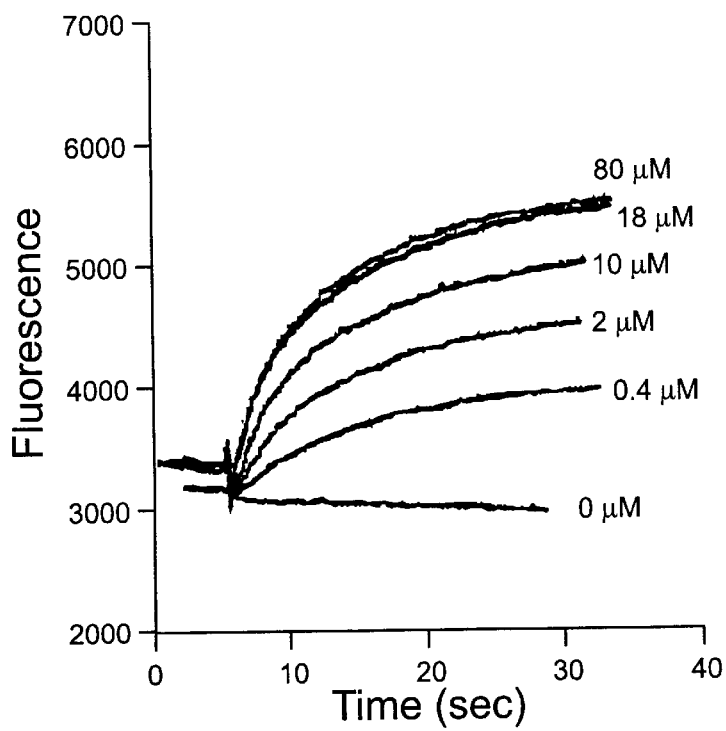
FIG. 10. Effect of Bax channel blocker.

Compound A inhibits Bax-induced release of carboxyfluorescein from liposomes: Liposomes have been incubated with different concentrations of compound A from 16 nM to 10 µM. After addition of the compound, 80 nM Bax was added to the liposome suspension and the fluorescence measured with a spectrofluorimeter. As shown in FIG. 10, compound A inhibits the release of carboxyfluorescein in a concentration dependent manner, with an IC50 of approximately 0.5 µM.

Compound A protects sympathetic neurons from NGF deprivation: Cultured sympathetic neurons undergo apoptosis when deprived of nerve growth factor (NGF). Compound A was added at different concentrations in the culture medium of five-day old sympathetic neurons and NGF was removed from the culture medium. Twenty-four hours later neuron survival was measured. All untreated neurons had undergone apoptosis. In contrast almost all neurons treated with 10 µM compound A survived. The IC50 was about 400 nM.

All documents cited above are hereby incorporated in their entirety by reference.

One skilled in the art will appreciate from a reading of this disclosure that various changes in form and detail can be made without departing from the true scope of the invention.

What is claimed is:

1. A method of testing a compound for its ability to modulate Bax protein channel formation or Bax protein channel activity comprising:
    contacting a lipid membrane selected from the group consisting of:
        (i) neuronal cell membranes,
        (ii) red blood cell membranes,
        (iii) mitochondrial membranes, and
        (iv) synthetic planar lipid bilayers or liposomes comprising phospholipids,
    with Bax protein in the presence of said compound,
        determining the level of Bax protein channel formation or Bax protein channel activity in said membrane, and
        comparing said level of Bax protein channel formation or Bax protein channel activity to a level of Bax protein channel formation or Bax protein channel activity in said membrane in the absence of said compound,
        wherein a higher or lower level of Bax protein channel formation or Bax protein channel activity in the presence of said compound, relative to the level of Bax protein channel formation or Bax protein channel activity in the absence of said compound, indicates that said compound modulates Bax protein channel formation or Bax protein channel activity.

2. The method of claim 1 wherein said method is a method of testing said compound for its ability to enhance Bax protein channel formation or Bax protein channel activity, wherein a higher level of Bax protein channel formation or Bax protein channel activity in the presence of said compound, relative to the level of Bx protein channel formation or Bax protein channel activity in the absence of said compound, indicates that said compound enhances Bax protein channel formation or Bax protein channel activity.

3. The method of claim 1 wherein said method is a method of testing said compound for its ability to inhibit Bax protein channel formation or Bax protein channel activity, wherein a lower level of Bax protein channel formation or Bax protein channel activity in the presence of said compound, relative to the level of Bax protein channel formation or Bax protein channel activity in the absence of said compound, indicates that said compound inhibits Bax protein channel formation or Bax protein channel activity.

4. The method according to claim 1 wherein said lipid membrane is a synthetic planar lipid bilayer comprising diphytaneoyl-phosphatidyl choline or diphytaneoyl-phosphatidylcholine and phosphatidylserine.

5. The method according to claim 1 wherein said lipid membrane is in the form of a liposome comprising phosphatidylserine, phosphatidylcholine and cholesterol.

6. The method according to claim 1 wherein said lipid membrane is a cellular lipid membrane or a lipid membrane of a cellular organelle selected from the group consisting of
    (i) neuronal cell membranes,
    (ii) red blood cell membranes, and
    (iii) mitochondrial membranes.

7. The method according to claim 6 wherein said cellular membrane is a membrane of an intact cell and said determining step is effected by monitoring lysis or death of said cell.

8. The method of claim 7 wherein said cell is a mammalian cell.

9. The method of claim 7 wherein said cell is a neuron or red blood cell.

10. The method of claim 6 wherein said lipid membrane is a mitochondrial membrane.

11. The method according to claim 1 wherein said determining step is effected by monitoring Bax channel-dependent passage of a detectable material through said lipid membrane.

12. The method according to claim 11 wherein said detectable material is a dye.

13. The method according to claim 12 wherein said dye is a fluorescent dye.

14. The method according to claim 11 wherein said lipid membrane is in the form of a liposome, said detectable material is encapsulated in said liposome and said liposome is present in a solution.

15. The method according to claim 14 wherein said detectable material is dye.

16. The method according to claim 15 wherein said dye is a fluorescent dye.

17. The method according to claim 16 wherein said dye is present in said liposome at a concentration such that the fluorescence thereof is quenched, and wherein said monitoring is effected by detecting an increase in fluorescence in said solution as said dye concentration in said solution increases.

18. The method of claim 1 wherein said Bax protein is mammalian Bax protein.

19. The method of claim 18 wherein said Bax protein is human Bax protein.

20. The method of claim 1 wherein said Bax protein is a soluble Bax protein.

21. The method according to claim 20 wherein said Bax protein is devoid of the C-terminal 20 amino acids forming the hydrophobic region of a naturally occurring Bax protein.

22. A synthetic lipid membrane selected from the group consisting of synthetic planar lipid bilayers and liposomes comprising phospholipids, comprising a channel therethrough wherein said channel is formed by Bax protein.

23. The membrane according to claim 22 wherein said channel comprises at least 2 Bax protein molecules.

24. The membrane according to claim 22 wherein said membrane is in the form of a liposome comprising phosphatidylserine, phosphatidylcholine and cholesterol.

25. A lipid membrane selected from the group consisting of:
   (i) neuronal cell membranes,
   (ii) red blood cell membranes,
   (iii) mitochondrial membranes, and
   (iv) synthetic planar lipid bilayers or liposomes comprising phospholipids,
comprising a channel therethrough wherein said channel is formed by a soluble Bax protein.

26. The membrane according to claim 25 wherein said membrane is in the form of a liposome comprising phosphatidylserine, phosphatidylcholine and cholesterol.

27. A kit comprising Bax protein and a lipid membrane selected from the group consisting of:
   (i) neuronal cell membranes,
   (ii) red blood cell membranes,
   (iii) mitochondrial membranes, and
   (iv) synthetic planar lipid bilayers or liposomes comprising phospholipids.

28. The kit according to claim 27 wherein the lipid membrane components are phospholipids.

29. A method of forming a channel in a synthetic lipid membrane selected from the group consisting of synthetic planar lipid bilayers and liposomes comprising phospholipids, comprising contacting said membrane with a Bax protein under conditions such that said Bax protein inserts into said membrane and forms said channel.

30. The method of claim 29 wherein said Bax protein is a soluble Bax protein.

31. The method of claim 29 wherein said membrane is in the form of a liposome comprising phosphatidylserine, phosphatidylcholine and cholesterol.

32. A method of forming a channel in a lipid membrane selected from the group consisting of:
   (i) neuronal cell membranes,
   (ii) red blood cell membranes,
   (iii) mitochondrial membranes, and
   (iv) synthetic planar lipid bilayers or liposomes comprising phospholipids
comprising contacting said membrane with a soluble Bax protein under conditions such that said soluble Bax protein inserts into said membrane and forms said channel.

33. The method according to claim 32 wherein said membrane is in the form of a liposome comprising phosphatidylserine, phosphatidylcholine and cholesterol.

34. A synthetic lipid membrane selected from the group consisting of synthetic planar lipid bilayers and liposomes comprising phospholipids comprising a channel therethrough wherein said channel is formed by Bax protein and Bcl-2 protein.

35. The membrane according to claim 34 wherein said membrane is in the form of liposome comprising phosphatidylserine, phosphatidylcholine and cholesterol.

36. A lipid membrane selected from the group consisting of:
   (i) neuronal cell membranes,
   (ii) red blood cell membranes,
   (iii) mitochondrial membranes, and
   (iv) synthetic planar lipid bilayers or liposomes comprising phospholipids
comprising a channel therethrough wherein said channel is formed by soluble Bax protein and Bcl-2.

37. A membrane according to claim 36 wherein said membrane is in the form of a liposome comprising phosphatidylserine, phosphatidylcholine and cholesterol.

38. A method of forming a channel in a synthetic lipid membrane selected from the group consisting of synthetic planar bilayers and liposomes comprising phospholipids, comprising contacting said membrane with Bax protein and Bcl-2 under conditions such that said Bax protein and Bcl-2 insert into said membrane and form said channel.

39. The method of claim 38 wherein said Bax protein is a soluble Bax protein.

40. A method of forming a channel in a lipid membrane selected from the group consisting of:
   (i) neuronal cell membranes,
   (ii) red blood cell membranes,
   (iii) mitochondrial membranes, and
   (iv) synthetic planar lipid bilayers or liposomes comprising phospholipids,
comprising contacting said membrane with soluble Bax protein and Bcl-2 under conditions such that said Bax protein and Bcl-2 insert into said membrane and form said channel.

41. A method of testing a compound for its ability to modulate formation or activity of a heteropore comprising Bax protein and Bcl-2 comprising:
   contacting a lipid membrane selected from the group consisting of:

(i) neuronal cell membranes,
(ii) red blood cell membranes,
(iii) mitochondrial membranes, and
(iv) synthetic planar lipid bilayers or liposomes comprising phospholipids, with Bax protein and Bcl-2 in the presence of said compound, determining the level of Bax protein/Bcl-2 heteropore formation or Bax protein/Bcl-2 heteropore activity in said membrane, and comparing said level of Bax protein/Bcl-2 heteropore formation or Bax protein/Bcl-2 heteropore activity to a level of Bax protein/Bcl-2 heteropore formation or Bax protein/Bcl-2 heteropore activity in said membrane in the absence of said compound, wherein a higher or lower level of Bax protein/Bcl-2 heteropore formation or Bax protein/Bcl-2 heteropore activity in the presence of said compound, relative to the level of Bax protein/Bcl-2 heteropore formation or Bax protein/Bcl-2 heteropore activity in the absence of said compound, indicates that said compound modulates Bax protein/Bcl-2 heteropore formation or Bax protein/Bcl-2 heteropore activity.

* * * * *

UNITED STATES PATENT AND TRADEMARK OFFICE
CERTIFICATE OF CORRECTION

PATENT NO. : 6,022,720
DATED : February 8, 2000
INVENTOR(S) : Martinou et al.

It is certified that error appears in the above-identified patent and that said Letters Patent is hereby corrected as shown below:

Item [75] Inventors: Jean-Claude Martinou; Remy Sadoul; Bruno Antonsson; all of Geneva, Switzerland, Franco Conti; Genova, Italy; Gonzola Mazzei; Geneva, Switzerland.

Signed and Sealed this

Twenty-eighth Day of August, 2001

*Attest:*

NICHOLAS P. GODICI
*Attesting Officer*     *Acting Director of the United States Patent and Trademark Office*